United States Patent [19]

Nadaud et al.

[11] Patent Number: 5,798,108
[45] Date of Patent: Aug. 25, 1998

[54] COSMETIC COMPOSITION IN THE FORM OF A WATER/OIL/WATER TRIPLE EMULSION WITH GELLED EXTERNAL PHASE

[75] Inventors: Jean Francois Nadaud, Paris; Laurence Sebillotte, Creteil, both of France

[73] Assignee: L'Oreal, France

[21] Appl. No.: 373,209

[22] PCT Filed: Jul. 13, 1993

[86] PCT No.: PCT/FR93/00714

§ 371 Date: Mar. 10, 1995

§ 102(e) Date: Mar. 10, 1995

[87] PCT Pub. No.: WO94/02120

PCT Pub. Date: Feb. 3, 1994

[30] Foreign Application Priority Data

Jul. 17, 1992 [FR] France ................... 92 08870

[51] Int. Cl.$^6$ ........................... A61K 7/00
[52] U.S. Cl. ........................... 424/401; 424/70.11; 510/119; 510/130; 514/847; 514/937; 524/501
[58] Field of Search ............... 424/401, 70.11, 424/70.19, 70.31; 514/937, 772.4, 847; 510/119, 121, 130, 137; 524/501

[56] References Cited

U.S. PATENT DOCUMENTS

| | | | |
|---|---|---|---|
| 4,254,105 | 3/1981 | Fukuda | 424/170 |
| 4,960,764 | 10/1990 | Figueroa, Jr. et al. | 514/938 |
| 5,306,498 | 4/1994 | Vesperini et al. | 424/401 |
| 5,322,689 | 6/1994 | Hughes et al. | 424/401 |
| 5,492,894 | 2/1996 | Bascom et al. | 514/18 |
| 5,534,246 | 7/1996 | Herb et al. | 424/66 |
| 5,567,426 | 10/1996 | Nadaud et al. | 424/401 |
| 5,576,064 | 11/1996 | Fructus | 424/401 |
| 5,589,177 | 12/1996 | Herb et al. | 424/401 |
| 5,612,043 | 3/1997 | Deprez et al. | 424/401 |
| 5,656,280 | 8/1997 | Herb et al. | 424/401 |

*Primary Examiner*—S. Mark Clardy
*Assistant Examiner*—Robert H. Harrison
*Attorney, Agent, or Firm*—Cushman Darby & Cushman IP Group of Pillsbury Madison & Sutro

[57] ABSTRACT

The invention discloses a gelled water/oil/water triple emulsion comprising: (A) a fatty phase comprising at least one wax having a melting point of at least 60° C. and forming the primary W/O emulsion with an aqueous phase; (B) a dilution oil; (C) a gelled continuous external aqueous phase comprising at least a gelling agent having a fatty chain of the monoethylene carboxylic acid or acid anhydride copolymer type with 3 to 6 carbon atoms or a fatty chain acrylic ester. In the triple emulsion, the amount of fatty phase from the W/O emulsion is from 1 to 30% and the amount of wax having a melting point of at least 60° C. is from 0.2 to 10%, based on the total weight of the triple emulsion. Said triple emulsion can be used as a carrier in cosmetic or dermatologically active compositions suitable for use on the skin or hair.

15 Claims, No Drawings

COSMETIC COMPOSITION IN THE FORM OF A WATER/OIL/WATER TRIPLE EMULSION WITH GELLED EXTERNAL PHASE

This application is a 371 of PCT/FR93/00714 filed Jul. 13, 1993.

The present invention relates to a cosmetic or dermatological composition provided in the form of a gelled water/oil/water triple emulsion, to a process for its preparation and to its applications in the cosmetic and dermatological fields.

Emulsions have been used for several years in products for the cosmetic treatment of the skin, especially in the cosmetics field. These emulsions are generally oil-in-water (O/W) or water-in-oil (W/O) emulsions.

Triple emulsions of the W/O/W type, or alternatively of the O/W/O type, are also used in cosmetics or in dermatology. However, such emulsions have many problems associated with their manufacture or alternatively problems of stability over time, especially when active substances which may have a tendency to destabilize the prepared emulsions are introduced into these emulsions.

Patent Application EP-A-0,345,075 (UNILEVER) describes W/O/W triple emulsions in which the continuous external phase is gelled and which contain an osmotic pressure agent in the internal aqueous phase, this agent attracting the water of the external phase through the oily phase. The process for preparing these gelled emulsions consists in dispersing a water-in-oil emulsion, the aqueous phase of which contains an osmotic pressure agent, in a solution of a gelling agent, of the polysaccharide, gelatin or other protein type. However, these emulsions have drawbacks. The osmotic pressure difference between the internal aqueous phase and the external aqueous phase causes water to leak from the external aqueous phase to the internal aqueous phase, and thus causes a swelling of the internal aqueous globules and a high concentration of gelling agent in the external aqueous phase, resulting in a product which is too gelatinous.

Patent Application EP-A-0,281,394 (RICHARDSON VICKS) relates to an O/W/silicone emulsion. This is a very specific emulsion, obtained by introduction of a standard O/W emulsion into a silicone-containing oily phase which constitutes the external oily phase. This emulsion contains various surface-active agents which act as emulsifiers in the O/W emulsion.

However, it is known that the use of a large amount of surface-active agents in an emulsion for cosmetic use may cause irritation or allergy-type skin reactions.

It should thus be sought to minimize the amounts of surface-active agents, while at the same time not destabilizing the emulsion.

The Applicant has succeeded in overcoming the difficulties, both technical and cosmetic, associated with the triple emulsions of the prior art and in obtaining a triple emulsion possessing a novel texture, advantageous cosmetic properties and good stability, without containing surfactant in the external phase.

The triple emulsion according to the invention is a gelled water/oil/water (W/O/W) emulsion, in which the water/oil primary emulsion is distributed homogeneously with globules between 0.5 and 50 μm in size, this imparting a smooth and shiny appearance thereto. The triple emulsion according to the invention is also gelled, creamy, fresh, soft, non-greasy and stable.

The subject of the invention is thus a triple emulsion having the characteristics defined below.

Another subject of the invention consists of the process for the preparation of such an emulsion.

A further subject of the invention is the cosmetic or dermatological use of such an emulsion.

Other subjects of the invention will become apparent on reading the description and the examples which follow.

The gelled water/oil/water triple emulsion in accordance with the invention is essentially charaterized in that it contains:

(A) a fatty phase comprising at least one wax with a melting point above or equal to 60° C., constituting with an aqueous phase the W/O primary emulsion;

(B) a dilution oil;

(C) a gelled continuous external aqueous phase comprising at least one fatty chain-containing gelling agent of the $C_3$–$C_6$ monoethylenic carboxylic acid or acid anhydride/fatty chain-containing acrylic ester copolymer type;

in which triple emulsion the amount of fatty phase derived from the W/O emulsion is between 1 and 30% and the amount of wax(es) with a melting point above or equal to 60° C. is between 0.2 and 10%, based on the total weight of the triple emulsion.

The gelled continuous external aqueous phase of the W/O/W triple emulsion according to the invention comprises water and a fatty chain-containing gelling agent of the type of a copolymer of a monoethylenic carboxylic acid containing 3 to 6 carbon atoms (or the anhydride thereof) and an acrylic ester containing a long chain.

This type of optionally crosslinked water-soluble acrylic copolymer, which will be referred to below as "fatty chain-containing gelling agent", is described in EP-A-0,268,164. In this copolymer, the proportion of monomer acid is preferably from 90 to 98% by weight and the proportion of monomer ester is preferably from 10 to 2% by weight.

The monomer acid has the formula:

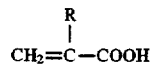

in which formula R represents H, a halogen, OH, a lactone or lactam radical, a group —C≡N or a $C_1$–$C_3$ alkyl radical. Acrylic acid and maleic anhydride are the preferred acid monomers.

The monomer ester has the formula:

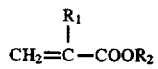

in which formula:

$R_1$ is H, methyl or ethyl, and $R_2$ is a $C_8$–$C_{30}$ alkyl radical or a $C_8$–$C_{30}$ oxyalkylene radical. $C_{10}$–$C_{22}$ alkyl radicals are preferred. Among the preferred monomer esters there may be mentioned: the decyl, lauryl, stearyl, behenyl and melissyl acrylates and methacrylates.

The copolymers used according to the invention are, at least in some cases, commercially available; they are, for example, marketed under the names PEMULEN and CARBOPOL 1342 by the company GOODRICH.

The gelled continuous external aqueous phase may additionally comprise other constituents, such as other gelling agents of the carboxyvinyl polymer type, for instance those sold under the names CARBOPOL 980 or 942 or 950, etc., by the company GOODRICH, or that sold under the name SYNTHRALEN K by the company SIGMA, polyglyceryl methacrylates sold by the company GUARDIAN under the name LUBRAJEL, carrageenans such as the product sold by the company SANOFI under the name SATIAGEL K80 (D-galactopyrannose sulfate), xanthan gums such as the xanthan/polysaccharides product comprising glucose/mannose/glucuronic acid (40/30/30) units, sold by the company KELCO under the name KELTROL.

The external aqueous phase may also contain glycols and neutralizing agents such as triethanolamine or sodium hydroxide. It may also contain preserving agents, dyes, fragrances, active agents, sunscreen agents, moisturizing agents such as glycerine and creaminess agents such as the product SEPIGEL 305 (polyacrylamide/C13-14 isoparaffin/Laureth-7) sold by the company SEPPIC.

The water-in-oil (W/O) primary emulsion used in the W/O/W triple emulsion according to the invention comprises a high level, above 35% by weight, of fatty phase containing at least one wax with a melting point above or equal to 60° C. and an aqueous phase, as well as one or more emulsifying agents.

The emulsifying agents contained in the W/O primary emulsion according to the invention may be chosen from the following surfactants:

Anionic surfactants such as fatty acid salts (for example metal salts or organic salts such as amine salts); these fatty acids have, for example, 12 to 18 carbon atoms and may contain a double bond, as in the case of oleic acid. There may, for example, be mentioned NOREMULSOL G5 sold by the company VERLEY (aluminum distearate/stearic acid/sodium sulfate/39/56/5 [sic]) and ALLUGEL 44M sold by the company BARLOCHER (aluminum stearate).

The other anionic surfactants are the alkali metal salts or organic-base salts of alkylsulfuric and alkylsulfonic acids having 12 to 18 carbon atoms, alkylarylsulfonic acids, the alkyl chain of which contains from 6 to 8 carbon atoms, ether sulfates, in particular the products of sulfation of polyalkoxylated alkylphenols and fatty alcohols in which the aliphatic chain contains from 6 to 20 carbon atoms and the polyalkoxylated chain contains from 1 to 30 oxyalkylene units, including oxyethylene, oxypropylene or oxybutylene.

The nonionic surfactants are mainly polyalkoxylated and/or polyglycerolated surfactants. They are in particular polyoxyethylenated, possibly polyoxypropylenated, derivatives. Polyalkoxylated and/or polyglycerolated fatty acids or fatty acid amides form part of this category. These are starting materials sold, for example, under the name MYRJ by the company ATLAS or PROTEGIN sold by the company GOLDSCHMIDT. When the polyol is sorbitol, the products sold under the name TWEEN or ARLACEL by the company ICI may be mentioned. The polyalkoxylated and/or polyglycerolated alkylphenols or fatty alcohols are sold by the company ATLAS under the name BRIJ.

The other nonionic surfactants are polyalkoxylated 1,2- or 1,3-alkanediols or -alkenediols, and polyalkoxylated and/or polyglycerolated 1,2- or 1,3-alkanediol or -alkenediol alkyl ethers.

The fatty alcohols or acids, which are optionally unsaturated, have 12 to 24 carbon atoms, the alkyl chain of the alkylphenols has 6 to 16 carbon atoms, the alkanediols or alkenediols have from 9 to 24 carbon atoms, the alkyl chain of the alkyl ethers has from 4 to 20 carbon atoms and the number of oxyalkylene units or of units ($CH_2CHOHCH_2O$) may range from 2 to 40.

Co-emulsifying agents which may be hydrogenated or unhydrogenated lecithins, or stabilizing agents, for instance inorganic salts such as magnesium sulfate and sodium chloride, may be added thereto.

The waxes with a melting point above 60° C. are, for example, fossil waxes including ozokerite, montan wax, waxes of animal origin including beeswax or waxes of plant origin including candellila wax and carnauba wax.

Waxes with a melting point below 60° C. such as mineral waxes including microcrystalline waxes, paraffin and vaseline, waxes of animal origin including spermaceti, lanolin and derivatives thereof (lanolin alcohol, hydrogenated lanolin, hydroxylated lanolin, acetylated lanolin, lanolin fatty acids and acetylated lanolin alcohol) may be added thereto.

Hydrogenated oils which are solid at 25° C., such as hydrogenated castor oil and hydrogenated tallow, and fatty esters which are solid at 25° C., such as propylene glycol monomyristate and myristyl myristate, may also be added to the fatty phase of the primary emulsion.

The oils which may be used in the primary emulsion are mineral oils such as paraffin oil and vaseline oil and mineral oils having a boiling point between 300° and 400° C.; oils of animal origin such as perhydrosqualene; plant oils such as sweet almond oil, calophyllum oil, palm oil, apricot kernel oil, avocado oil, jojoba oil, olive oil, castor oil and cereal germ oils; synthetic oils, for instance fatty acid esters such as purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate and propylene glycol dicaprylate; esters derived from lanolic acid such as isopropyl lanolate and isocetyl lanolate; other oils such as acetylglycerides, alcohol and polyalcohol octanoates and decanoates such as those of glycol and of glycerol, and alcohol and polyalcohol ricinoleates such as those of cetyl.

The primary emulsion may also contain fatty alcohols such as oleyl alcohol, isostearyl alcohol, cetyl alcohol, stearyl alcohol and octyldodecanol.

The fatty phase of the W/O primary emulsion may also contain lipophilic additives usually used in cosmetics, for example active substances and sunscreen agents.

The aqueous phase of the W/O primary emulsion comprises water and may contain a moisturizing agent such as glycerine, a polyol such as propylene glycol, hexylene glycol, dipropylene glycol and 1,3-butylene glycol. It may also contain the usual additives such as preserving agents, fragrances and dyes, as well as active agents and sunscreen agents.

The Applicant has observed that the addition of compounds containing organofluorine groups and hydrocarbon groups to the W/O primary emulsion makes it possible to reduce the sticking effect caused by the fatty chain-containing gelling agent contained in the external aqueous phase, and makes it possible to provide the finished product with greater softness and creaminess.

These compounds containing organofluorine groups and hydrocarbon groups have a chemical structure comprising a carbon skeleton in which certain hydrogen atoms have been substituted with fluorine atoms, the carbon skeleton possibly comprising one or more hetero atoms and one or more organic functional groups.

For the compounds containing organofluorine groups and hydrocarbon groups, the degree of substitution of the hydrogen atoms with fluorine atoms is defined by the ratio: number of fluorine atoms/(number of fluorine atoms+ number of hydrogen atoms) where only the hydrogen atoms bonded to the carbon atoms of the skeleton are taken into account. The compounds containing organofluorine groups and hydrocarbon groups used in the emulsions according to the invention contain at least one hydrocarbon group in the molecule.

These compounds containing organofluorine groups which are used according to the invention preferably have a degree of substitution between 0.5 and 95%. This degree is preferably greater than 10% and less than 80%.

The compounds containing organofluorine groups and hydrocarbon groups which are used according to the present invention have the following formula:

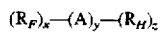

in which:

x represents 1, 2 or 3,
y represents 0 or 1,
z represents 0, 1, 2 or 3, on condition that y and z are not simultaneously 0, and that when z is 0, x is 2 or 3.

$R_F$ represents a saturated or unsaturated aliphatic or aromatic fluoro radical containing a linear, branched or cyclic chain, this chain possibly being functionalized and/or interrupted by divalent atoms such as oxygen or sulfur, or trivalent atoms such as nitrogen, and/or substituted with hydrogen atoms or other halogen atoms, on condition that not more than one of these substituents, other than fluorine, is present for two carbon atoms of the chain.

$R_H$ represents a saturated or unsaturated aliphatic or aromatic hydrocarbon radical containing a linear, branched or cyclic chain, this chain possibly being functionalized and/or interrupted by one or more divalent atoms such as oxygen or sulfur or by one or more trivalent atoms such as nitrogen.

A represents a di-, tri- or quadrivalent radical such as:

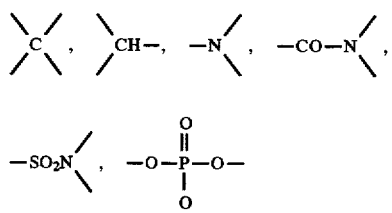

as well as the aliphatic or aromatic cyclic structures comprising such a radical, or ethylenic unsaturations.

According to the invention, the expression "functionalized" is understood to mean an intercalated, terminal or pendant substitution of the skeleton by at least one organic functional group such as an alcohol, thiol, acid, carbonyl, sulfoxide, ester, amide, amine, phosphate, ethylenic, acetylenic, enamine or sulfonamide function.

The term ethylenic unsaturation is understood to mean, for example:

$R_H$ preferably represents a linear or branched $C_1$–$C_{22}$ alkyl radical or a mixture of linear or branched $C_1$–$C_{22}$ alkyl radicals, a $C_6$–$C_{10}$ aryl radical or a $C_7$–$C_{15}$ aralkyl radical.

$R_F$ preferably represents a perfluoroalkyl radical having from 4 to 22 carbon atoms.

As an illustration, there may be mentioned compounds possessing perfluorocarbon groups and hydrocarbon groups, the total number of carbon atoms being between 10 and 30, the number of carbon atoms of the hydrocarbon groups being equal to or greater than twice the number of carbon atoms of the perfluorocarbon groups as are described in the document JP 63-002916.

Similarly, as a guide, there may be mentioned the organofluorine hydrocarbon compounds whose general structure is defined by the formula:

where $C_3H_5$ (OH) represents:

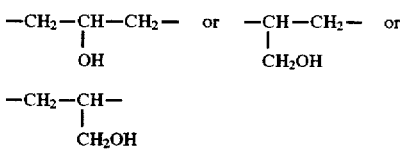

$R_1$ represents a linear or branched $C_4$–$C_{20}$ perfluoroalkyl radical or a mixture of linear or branched $C_4$–$C_{20}$ perfluoro [lacuna] radicals, $R_2$ represents a linear or branched $C_1$–$C_{22}$ alkyl radical or a mixture of linear or branched $C_1$–$C_{22}$ alkyl radicals or a $C_6$–$C_{10}$ aryl radical or a $C_7$–$C_{15}$ aralkyl radical.

X and Y, which may be identical or different, represent:

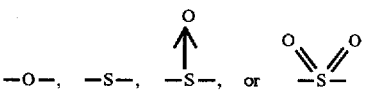

with the proviso that X and Y do not simultaneously represent

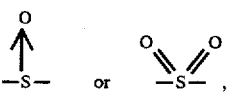

n is between 0 and 4, and
x represents 0 or 1.

These compounds used according to the invention are described in FR-A 2,684,668 and EP-A-166,696.

Moreover, it is also possible, according to the invention, to use the compounds of formula:

in which $C_3H_5$ (OH) represents the structures:

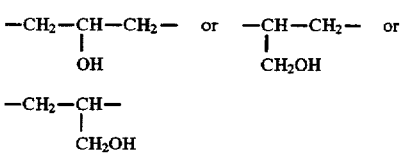

$R_F$ and $R'_F$, which may be identical or different, represent a linear or branched $C_4$–$C_{20}$ perfluoroalkyl radical or a mixture of linear or branched $C_4$–$C_{20}$ perfluoroalkyl radicals;

m and n, which may be identical or different, represent 0, 1, 2, 3 or 4;

X and Y, which are identical, are —O— or —S—.

These compounds are described in DE-2,702,607, JP 89-193,236, JP 92-275,268 and U.S. Pat. No. 3,893,984.

It is also possible, according to the invention, to use the compounds described in the document U.S. Pat. No. 3,952,066, of formula:

$$R_f-CH_2-CH_2-X-CH_2-\underset{\underset{Y}{|}}{CH}-Z$$

where Y is OH, and
Z is

—⟨phenyl⟩, —CH$_3$, —CH$_2$OH, —CH$_2$OCOCH$_3$ or alternatively Y is —CH$_2$OH and Z is —O—COCH$_3$
X represents —O—, —S—, —S(=O)— or —S(=O)$_2$—, and R$_f$ represents a linear or branched C$_4$–C$_{20}$ perfluoroalkyl radical or a mixture of linear or branched C$_4$–C$_{20}$ perfluoroalkyl radicals;

or alternatively the compounds described in the document DE 2,052,579, of formula:

$$R_f-CH=CH-CH_2-O-CH_2-[C_2H_4-OW]$$

where
C$_2$H$_4$OW denotes:

—CH(OH)—CH$_2$W   or   —CH(W)—CH$_2$OH (a)   (b)

W denoting:

—OR, —SR, —COOR, —O—⟨phenyl⟩,

—O—⟨phenyl-R'⟩

R denotes a linear or branched C$_1$–C$_{18}$ alkyl radical,
R' denotes —CH$_3$ or —OH, in the ortho or para position, and R$_f$ represents a linear or branched C$_4$–C$_{20}$ perfluoroalkyl radical or a mixture of linear or branched C$_4$–C$_{20}$ perfluoroalkyl radicals.

The primary emulsion is diluted with an oil cited above before dispersing it into the gelled continuous external aqueous phase, in order to obtain the stable final triple emulsion.

By working in this way, the size of the globules of the triple emulsion is between 0.5 and 50 μm.

The triple emulsion of the present invention contains 0.02 to 0.7% by weight of W/O emulsifying agent(s), 0.2 to 10% by weight of wax(es) with a melting point above or equal to 60° C., 5 to 20% by weight of oil(s), 0.5 to 20% by weight of wax(es) with a melting point below 60° C., 0.1 to 3% by weight of fatty chain-containing gelling agent, neutralizing agents (triethanolamine and sodium hydroxide), and the co-emulsifying agents for the primary emulsion which are indicated above, and optionally cosmetological or dermatological active substances, as well as other adjuvants usually used in cosmetics such as preserving agents, dyes, fragrances, moisturizing agents and sunscreen agents, the remainder consisting of water.

Another subject of the invention is the process for preparing a triple emulsion according to the invention.

In a first step, the water-in-oil primary emulsion is prepared by adding an aqueous phase to the fatty phase, in order to obtain a W/O emulsion.

In a second step, the primary emulsion thus obtained is diluted, before its dispersion into the gelled aqueous phase, with an oil as cited above, which may be identical to or different from that used in the primary emulsion.

In a third step, the triple emulsion is prepared by adding the primary emulsion thus diluted with an oil to a second gelled aqueous phase which constitutes the external aqueous phase of the emulsion.

As already indicated above, the compositions in triple emulsion form in accordance with the invention exhibit particularly noteworthy cosmetic properties, especially as regards the feel and the appearance, which allows them to be used as bases for applying the cosmetic active substances to the skin.

The introduction of active substances into the internal and/or external aqueous phase and/or into the oily phase makes possible many uses of such a triple emulsion.

These emulsions may be used in particular in facial care products for dry skins or for greasy skins. In order to prepare products for dry skins, water-soluble moisturizing active substances such as, for example, glycerine, propylene glycol, sorbitol, proline, pyrrolidone-carboxylic acid and derivatives thereof, urea, hydrolyzed collagen, Aloe vera gel, hyaluronic acid and derivatives thereof, dimethylsilanol hyaluronate and allantoin may be introduced into either of the two aqueous phases.

Treatment products for greasy skins are obtained by introducing into either of the two aqueous phases water-soluble active substances such as provitamin B5, which is used as an emollient, or an antibacterial agent such as transthiolane-3,4-diol S-dioxide.

The emulsions according to the invention may also be used as make-up removal products or facial cleansing products in the form of creams, milks or masks for example, or as make-up products by incorporation of fillers or pigments.

These emulsions may also be used as suntan products by introduction of screening agents.

As water-soluble sunscreen agents which may be introduced into the internal and/or external aqueous phase, 2-hydroxy-4-methoxybenzophenone 5-sulfonic acid sold under the name UVINUL MS 40 by the company BASF may, for example, be used. As lipid-soluble sunscreen agents to be introduced into the oily phase, 2-ethylhexyl paramethoxycinamate [sic] sold under the name PARSOL MCX by the company GIVAUDAN or 2-hydroxy-4-methoxybenzophenone sold under the name UVINUL M 40 by the company BASF may, for example, be used.

The emulsions according to the invention may also be used in the preparation of after-sun products containing, for example, vitamin F and the moisturizing agents cited above as soothing active agents.

By introducing water-soluble or lipid-soluble slimming active substances into one of the two aqueous phases or into the fatty phase respectively, it is also possible to obtain slimming products.

Among the water-soluble slimming active substances which may be mentioned are xanthine derivatives such as caffeine, theobromine, theophylline, L-carnitine, dimethylaminoethyl theophylline hydrochloride, silicon derivatives of the methylsilanol theophyllinacetate-alginate type or plant derivatives such as aqueous-glycolic extracts of English ivy, of brown algae and of fresh wild pansy. Among the lipid-soluble slimming active substances which may be mentioned are D,L-alpha-tocopherol nicotinate, the oily extract of ginseng root (Panax ginseng), the oily extract of English ivy (Hedera helix), the oily extract of dried arnica flowers (Arnica montana L) and the oily extract of algae (Fucus vesiculosus).

By introducing moisturizing agents cited above and plant or mineral oils, body care products may also be obtained, as may hair products which are used, for example, to make the hair smooth, by introducing sunscreen agents in order to protect the hair from UV radiation.

The triple emulsions of the invention may also be used as products for heaviness in the legs, containing Ginkgo biloba, sweet clover or butcher's-broom as water-soluble active agents and standard oils as emollients.

The examples which follow are intended to illustrate the invention without, however, being limiting in nature.

FORMULATION EXAMPLES

Example 1

| FACIAL CARE CREAM (W/O/W) | |
|---|---|
| PHASE A (W/O) | |
| *LIQUID PARAFFIN | 2.7 g |
| *WHITE PETROLEUM JELLY | 2 g |
| LANOLIN (STELLA COMPANY) | 0.8 g |
| PURE BEESWAX | 1.05 g |
| *NOREMULSOL G5 ® (Anionic surfactant) (VERLEY COMPANY) | 0.1 g |
| CHOLESTEROL | 0.08 g |
| LECITHIN | 0.06 g |
| HYDROGENATED LECITHIN | 0.07 g |
| WATER | 3.14 g |
| PHASE B | |
| *LIQUID PURCELLIN OIL 2/066210 ® (DRAGOCO COMPANY) | 10 g |
| PHASE C | |
| *CARBOPOL 1342 ® (GOODRICH COMPANY) | 0.6 g |
| *TRIETHANOLAMINE | 0.6 g |
| *GLYCERINE | 3 g |
| PRESERVING AGENTS, FRAGRANCES, DYES | qs |
| DISTILLED WATER | qs 100 g |

*cf. annex describing the starting materials.

In order to prepare the triple emulsion, phase A is prepared, then phase B is added thereto and the mixture obtained is dispersed in phase C.

A panel of 34 women judged the cream to be pleasant, comfortable, of novel texture, non-greasy and soft.

Example 2

| BODY CARE MILK (W/O/W) | |
|---|---|
| PHASE A (W/O) | |
| *LIQUID PARAFFIN | 1.61 g |
| *WHITE PETROLEUM JELLY | 1.2 g |
| OZOKERITE | 0.63 g |

| BODY CARE MILK (W/O/W) -continued | |
|---|---|
| *NOREMULSOL G5 ® (Anionic Surfactant) | 0.06 g |
| LECITHIN | 0.04 g |
| HYDROGENATED LECITHIN | 0.04 g |
| WATER | 3.21 g |
| PHASE B | |
| *LIQUID PARAFFIN | 10 g |
| PHASE C | |
| *PEMULEN TR2 ® (GOODRICH COMPANY) | 0.5 g |
| *GLYCERINE | 5 g |
| *TRIETHANOLAMINE | 0.5 g |
| PRESERVING AGENTS, FRAGRANCES, DYES | qs |
| DISTILLED WATER | qs 100 g |

In order to prepare the triple emulsion, phase A is prepared, it is diluted in phase B and this is then dispersed in phase C.

The triple emulsion is in the form of a fresh, creamy, shiny fluid milk.

Example 3

| SLIMMING BODY CARE CREAM (W/O/W) | |
|---|---|
| PHASE A (W/O) | |
| *LIQUID PARAFFIN | 1.7 g |
| OZOKERITE | 1.2 g |
| CARNAUBA WAX | 1 g |
| *WHITE PETROLEUM JELLY | 2.5 g |
| *NOREMULSOL G5 ® (Anionic surfactant) | 0.12 g |
| LECITHIN | 0.18 g |
| WATER | 3.3 g |
| PHASE B | |
| SWEET ALMOND OIL | 10 g |
| PHASE C | |
| *PEMULEN TR1 ® (GOODRICH COMPANY) | 0.6 g |
| *CAFFEINE | 0.5 g |
| *TRIETHANOLAMINE | 0.6 g |
| PRESERVING AGENTS, DYES | qs |
| FRAGRANCES, ANTIOXIDANTS | qs |
| DISTILLED WATER | qs 100 g |

In order to prepare the triple emulsion, phase A is prepared, it is diluted in phase B and the preparation obtained is then dispersed in phase C.

A fresh cream is obtained, which spreads and penetrates well and which permits massaging.

Example 4

| MASK FOR FACIAL CARE (W/O/W) | |
|---|---|
| PHASE A (W/O) | |
| PROTEGIN X (Nonionic surfactant) (GOLDSCHMIDT COMPANY) | 1.9 g |
| ALLUGEL 44 M (Anionic surfactant) (BARLOCHER COMPANY) | 0.05 g |
| OZOKERITE | 1.4 g |
| *WHITE PETROLEUM JELLY | 2.5 g |
| MAGNESIUM SULFATE | 0.04 g |
| *GLYCERINE | 0.3 g |
| WATER | 3.81 g |

MASK FOR FACIAL CARE (W/O/W)

| PHASE B | |
|---|---|
| APRICOT KERNEL OIL | 10 g |
| PHASE C | |
| *CARBOPOL 1342 ® (GOODRICH COMPANY) | 0.7 g |
| *GLYCERINE | 3 g |
| SODIUM HYDROXIDE | 0.6 g |
| PRESERVING AGENTS, DYES | qs |
| FRAGRANCES, ANTIOXIDANTS | qs |
| DISTILLED WATER | qs 100 g |

In order to prepare the triple emulsion, phase A is prepared, it is diluted in phase B and the whole mixture is then dispersed in phase C.

A gelled cream is obtained which, on application to the face, gives a moisturizing mask which may be removed after 5 to 10 minutes.

Example 5

BODY CARE CREAM (W/O/W)

| PHASE A (W/O) | |
|---|---|
| 1-(2'-F-hexylethylthio)-3-(2"-ethylhexyloxy)-2-propanol | 1 g |
| *LIQUID PARAFFIN | 2.7 g |
| *WHITE PETROLEUM JELLY | 2 g |
| LANOLIN (STELLA COMPANY) | 0.8 g |
| PURE BEESWAX | 1.05 g |
| *NOREMULSOL G5 ® (VERLEY COMPANY) | 0.1 g |
| CHOLESTEROL | 0.08 g |
| LECITHIN | 0.06 g |
| HYDROGENATED LECITHIN | 0.07 g |
| WATER | 2.14 g |
| PRASE B | |
| *LIQUID PURCELLIN OIL 2/066210 ® (DRAGOCO COMPANY) | 10 g |
| PHASE C | |
| *CARBOPOL 1342 ® (GOODRICH COMPANY) | 0.6 g |
| *TRIETHANOLAMINE | 0.6 g |
| GLYCERINE | 3 g |
| PRESERVING AGENT(S), FRAGRANCE(S) DYE(S) | qs |
| WATER | qs 100 g |

Example 6

FACIAL CARE CREAM (W/O/W)

| PHASE A (W/O) | |
|---|---|
| *LIQUID PARAFFIN | 1.7 g |
| OZOKERITE | 1.2 g |
| CARNAUBA WAX | 1 g |
| *WHITE PETROLEUM JELLY | 2.5 g |
| *NOREMULSOL G5 ® (VERLEY COMPANY) | 0.12 g |
| LECITHIN | 0.18 g |
| WATER | 3.3 g |
| PHASE B | |
| SWEET ALMOND OIL | 10 g |
| PHASE C | |
| *PEMULEN TR1 ® R (GOORICH COMPANY) | 0.6 g |
| *CAFFEINE | 0.5 g |

FACIAL CARE CREAM (W/O/W)

| *TRIETHANOLAMINE | 0.6 g |
|---|---|
| PRESERVING AGENT(S), DYE(S) | qs |
| FRAGRANCE(S), ANTIOXIDANT(S) | qs |
| POLYACRYLAMIDE/C$_{13}$–C$_{14}$ ISOPARAFFIN/LAURETH 7 (SEPIGEL 305 from the SEPPIC COMPANY) | 1 g |
| WATER | qs 100 g |

Example 7

CARE CREAM FOR THE NECK (W/O/W)

| PHASE A (W/O) | |
|---|---|
| *LIQUID PARAFFIN | 1.61 g |
| *WHITE PETROLEUM JELLY | 1.2 g |
| OZOKERITE | 0.63 g |
| *NOREMULSOL GS ® (VERLEY COMPANY) | 0.06 g |
| LECITHIN | 0.04 g |
| HYDROGENATED LECITHIN | 0.04 g |
| WATER | 3.61 g |
| PHASE B | |
| *LIQUID PARAFFIN | 10 g |
| PHASE C | |
| *CARBOPOL 1342 ® (GOORICH COMPANY) | 0.5 g |
| CARBOMER (CTFA name) (SYNTHALEN K ® from the SIGMA COMPANY) | 0.5 g |
| *GLYCERINE | 5 g |
| *TRIETHANOLAMINE | 1 g |
| PRESERVING AGENT(S), FRAGRANCE(S) | qs |
| DYE(S) | qs |
| WATER | qs 100 g |

ANNEX - STARTING MATERIALS

| | |
|---|---|
| PURE GLYCERINE CODEX ®: STEARINERIE DUBOIS Company | Glycerine |
| CARBOPOL 980 ®: GOODRICH Company | Carboxyvinyl polymer synthesized in an ethyl acetate/cyclohexane mixture |
| 99% TRIETHANOLAMINE ®: B.P. Company | Triethanolamine |
| SATIAGEL K 80 ®: SANOFI Company | Pure carrageenan (D-galactopyrannose sulfate) (CTFA name: carrageenan) |
| KELTROL ®: KELCO Company | Xanthan/polysaccharides: glucose/mannose/glucuronic acid (40/30/30) |
| LUBRAJEL MS ®: GUARDIAN Company | Polyglyceryl methacrylate, glycerine, propylene glycol, water (3%/47%/1%/48.8%) |
| LIQUID PURCELLIN OIL: 2/066210 - DRAGOCO Company: | Isopropyl myristate cetearyl octanoate (10/90) |
| CARBOPOL 1342 ®: GOODRICH Company | Acrylic acid/C$_{10}$–C$_{30}$ alkyl acrylate copolymer (CTFA name: Acrylates/C$_{10}$–C$_{30}$ alkylacrylate crosspolymer) |
| CAFFEINE ®: PROLABO Company | Caffeine |
| MEXORYL SN ®: CHIMEX Company | Thiolanediol = trans-thiolane-3,4-diol S-dioxide |
| PEMULEN TR 1 ®: GOODRICH Company | Acrylic acid/C$_{10}$–C$_{30}$ alkyl acrylate copolymer (CTFA |

-continued

ANNEX - STARTING MATERIALS

| | |
|---|---|
| PEMULEN TR 2 ®:<br>GOODRICH Company | name: acrylates/$C_{10}$-$C_{30}$ alkylacrylate crosspolymer)<br>Acrylic acid/$C_{10}$-$C_{30}$ alkyl acrylate copolymer (CTFA name: acrylates/$C_{10}$-$C_{30}$ alkylacrylate crosspolymer) |
| SIDEPALINE BC 115 ®:<br>GEERAERT-MATTHYS Company | Liquid paraffin |
| WHITE PETROLEUM JELLY ®:<br>(Drop point 520)<br>AIGLON Company | Petroleum jelly |
| NOREMULSOL G5 ®:<br>VERLEY Company | Stearic acid, aluminum distearate, sodium sulfate (56/39/5) |
| PRODUCT AB ®:<br>SEPPIC Company | Bovid marrow lecithin |
| ALLUGEL 44M ®:<br>BARLOCHER Company | Aluminum stearate |
| PROTEGIN X ®:<br>GOLDSCHMIDT Company | Mineral oil/petroleum jelly/ozokerite/glyceryl oleate/lanolin alcohol |
| LECINOL S10:<br>(NIKKOL) | Hydrogenated lecithin |

We claim:

1. Gelled water/oil/water triple emulsion, which contains:
(A) a fatty phase comprising at least one wax with a melting point above or equal to 60° C., constituting with an aqueous phase the W/O primary emulsion;
(B) a dilution oil which is added to the W/O primary emulsion;
(C) a gelled continuous external aqueous phase without surfactant comprising at least one fatty chain-containing gelling agent which is a copolymer of a monoethylenic carboxylic acid containing 3-6 carbon atoms (or the anhydride thereof) and an acrylic ester containing a long chain selected from the group consisting of a $C_8$-$C_{30}$ alkyl radical and $C_8$-$C_{30}$ oxyalkylene radical;
wherein the amount of fatty phase in the W/O primary emulsion is greater than 35% by weight and the amount of wax(es) with a melting point above or equal to 60° C. is between 0.2 and 10%, based on the total weight of the triple emulsion.

2. Triple emulsion according to claim 1, wherein the gelled external aqueous phase additionally contains another gelling agent selected from the group consisting of carboxyvinyl polymers, polyglyceryl methacrylates, carrageenans and xanthan gums.

3. Triple emulsion according to claim 1, wherein the gelled external aqueous phase additionally contains glycols, neutralizing agents, preserving agents, dyes, fragrances, active substances, sunscreen agents, moisturizing agents or polyacrylamide/C13-14 isoparaffin/Laureth-7.

4. Triple emulsion according to claim 1, wherein the fatty phase of the W/O primary emulsion additionally comprises waxes with a melting point below 60° C. selected from the group consisting of mineral waxes, waxes of animal origin, and lanolin or derivatives thereof, hydrogenated oils which are solid at 25° C., mineral oils, oils of animal origin, plant oils, fatty acid esters, esters derived from lanolic acid and fatty alcohols.

5. Triple emulsion according to claim 1, wherein the aqueous phase of the primary emulsion comprises, in addition to water, moisturizing agents, polyols, active substances, preserving agents, sunscreen agents, fragrances and dyes.

6. Triple emulsion according to claim 1 wherein the W/O primary emulsion comprises at least one emulsifying agent selected from the group consisting of anionic surfactants, which are the metal salts or the organic salts of fatty acids containing 12 to 18 carbon atoms, the alkali metal salts or the organic-base salts of alkylsulfuric and alkylsulfonic acids containing 12 to 18 carbon atoms, alkylarylsulfonic acids, the alkyl chain of which contains 6 to 8 carbon atoms, or ether sulfates, polyalkoxylated nonionic surfactants and polyglycerolated nonionic surfactants.

7. Triple emulsion according to claim 1, wherein the W/O primary emulsion contains a co-emulsifying agent which is a hydrogenated or undhydrogenated lecithin, or a stabilizing inorganic salt.

8. Triple emulsion according to claim 1, wherein the W/O primary emulsion contains at least one compound containing organofluorine groups and hydrocarbon groups.

9. Triple emulsion according to claim 8, wherein the compound containing organofluorine groups and hydrocarbon groups has a degree of substitution of between 0.5 and 95%.

10. Triple emulsion according to claim 1 wherein the dilution oil is selected from the group consisting of mineral oils, oils of animal origin, plant oils, fatty acid esters and esters derived from lanolic acid.

11. Triple emulsion according to claim 1 which comprises, relative to the total weight of the triple emulsion, 0.02 to 0.7% by weight of W/O emulsifying agent(s), 0.2 to 10% by weight of wax(es) with a melting point above or equal to 60° C., 5 to 20% by weight of oil(s), 0.5 to 20% by weight of wax(es) with a melting point below 60° C., 0.1 to 3% of fatty chain-containing gelling agent, neutralizing agents, co-emulsifying agents for the primary emulsion, optionally cosmetological or dermatological active substances and cosmetic adjuvants, the remainder consisting of water.

12. Cosmetic composition to be applied to the skin or to the hair, which comprises a triple emulsion as defined in claim 1.

13. Composition to be used in dermatology and containing dermatologically active agents, which comprises a vehicle consisting of a triple emulsion as defined in claim 1.

14. Process for the preparation of a gelled water/oil/water triple emulsion according to claim 1, wherein in a first step, the W/O primary emulsion is prepared by adding an aqueous phase to a fatty phase containing at least one wax with a melting point above or equal to 60° C., in a second step, the primary emulsion obtained above is diluted with an oil which is identical to or different from that used in the primary emulsion and, finally, the triple emulsion is prepared by adding the diluted primary emulsion obtained above to a second gelled continuous external aqueous phase without surfactant containing a fatty chain-containing gelling agent which is a copolymer of a monoethylenic carboxylic acid containing 3-6 carbon atoms (or the anhydride thereof) and an acrylic ester containing a long chain selected from the group consisting of a $C_8$-$C_{30}$ alkyl radical and $C_8$-$C_{30}$ oxyalkylene radical; in which triple emulsion the amount of wax with a melting point above or equal to 60° C. is between 0.2 and 10% by weight, and the amount of fatty phase in the W/O primary emulsion is greater than 35% by weight, based on the total weight of the triple emulsion.

15. Process according to claim 14, wherein at least one of cosmetic adjuvant and one active substance are introduced into any of the phases constituting the tripe emulsion or into the final triple emulsion after preparation thereof.

* * * * *